United States Patent [19]

Kano et al.

[11] Patent Number: 4,563,430

[45] Date of Patent: Jan. 7, 1986

[54] METHOD OF JUDGING A PARTICLE AGGLUTINATION PATTERN

[75] Inventors: Tokio Kano, Kunitachi; Akira Tamagawa, Hino; Masanori Doi, Akishima, all of Japan

[73] Assignee: Olympus Optical Company Limited, Tokyo, Japan

[21] Appl. No.: 555,483

[22] Filed: Nov. 28, 1983

[30] Foreign Application Priority Data

Nov. 29, 1982 [JP] Japan ................... 57-209147

[51] Int. Cl.$^4$ .................. G01N 21/75; G01N 33/54
[52] U.S. Cl. ..................... 436/164; 356/442; 422/73; 436/518; 436/805
[58] Field of Search ............... 422/73; 436/805, 578, 436/34, 164; 356/39, 427, 434, 436, 440, 442, 444; 73/64.1

[56] References Cited

U.S. PATENT DOCUMENTS

| | | | |
|---|---|---|---|
| 3,520,609 | 7/1970 | Lion | 356/39 |
| 3,883,308 | 5/1975 | Matte | 422/67 X |
| 4,197,088 | 4/1980 | Meserol et al. | 422/73 X |
| 4,447,396 | 5/1984 | Kano | 422/73 |
| 4,452,759 | 6/1984 | Takekawa | 422/73 |
| 4,452,902 | 6/1984 | Suovaniemi et al. | 422/73 X |

FOREIGN PATENT DOCUMENTS 0046430 2/1982 European Pat. Off. .
3033870 4/1981 Fed. Rep. of Germany ........ 422/73

Primary Examiner—Arnold Turk
Attorney, Agent, or Firm—Parkhurst & Oliff

[57] ABSTRACT

In a method of photoelectrically judging a particle agglutination pattern formed on a conical bottom surface of a reaction vessel by particles descending upon the bottom surface, at least two judging steps utilizing a total particle amount, a thickness ratio, an inclination and so on are applied to the particle agglutination pattern to judge finally the pattern as one of an integral pattern (−), an intermediate pattern (?) and a uniform deposition pattern (+). In this manner, since all the inaccurate patterns are judged finally as the intermediate pattern (?) and are re-examined, it is possible to always perform an accurate judgment for the particle agglutination pattern.

11 Claims, 21 Drawing Figures

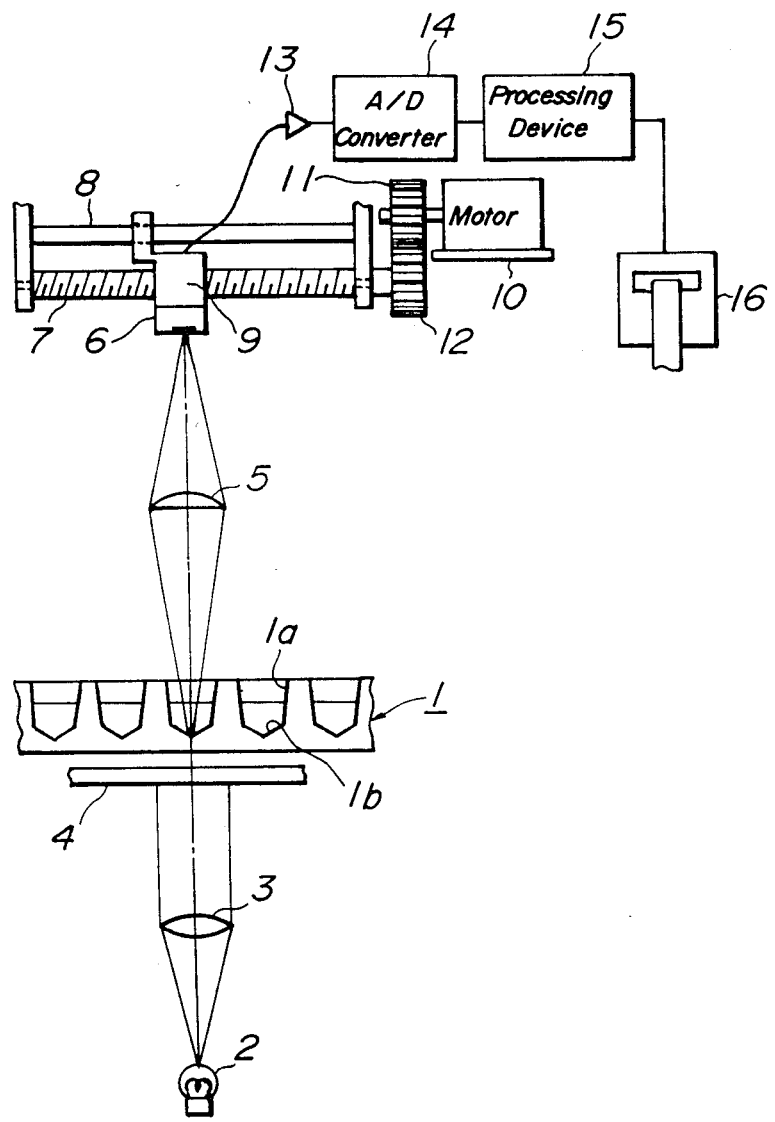
FIG_7

METHOD OF JUDGING A PARTICLE AGGLUTINATION PATTERN

BACKGROUND OF THE INVENTION

The present invention relates to a method for judging a particle agglutination pattern formed on an inclined bottom surface of a reaction vessel by particles descending upon the bottom surface.

There has been proposed in, for instance, Japanese Patent Application Laid-open Publication No. 2,564/81, a method for judging a particle agglutination pattern formed on an inclined conical bottom surface of a reaction vessel by projecting images of central and peripheral portions of the bottom, onto first and second light receiving elements, respectively and by suitably processing outputs of the light receiving elements. In the case of using the reaction vessel having the conical bottom, when the agglutination reaction occurs between the particles in a reaction liquid contained in the vessel, the particles are agglutinated with each other and are uniformly deposited on the inclined bottom surface like snow to form a so-called uniform deposition pattern, whilst when the non-agglutination reaction occurs, the particles descending on the bottom roll down along the inclined bottom surface and are collected to form a so-called integral pattern. Now it is assumed that the output of the first light receiving element receiving the image of the central bottom portion is $E_1$ and that of the second light receiving element receiving the image of the peripheral bottom portion is $E_2$. Then, a difference $\Delta E = |E_2 - E_1|$ between these outputs $E_1$ and $E_2$ changes in accordance with the particle agglutination pattern. That is to say, when the particles descending upon the bottom surface form the clear uniform deposition pattern illustrated in FIGS. 1A and 1B and having a distribution of the particle amount shown in FIG. 1C, the difference $\Delta E$ becomes extremely small. Contrary to this, when the clear integration pattern shown in FIGS. 2A, 2B and 2C is formed, the difference $\Delta E$ becomes large. Therefore, by comparing the difference $\Delta E$ with two reference values $V_1$ and $V_2$ ($V_1 > V_2$) which can be obtained experimentally, it is possible to judge the agglutination reaction in such a manner that if $\Delta E < V_2$ (FIG. 1), the pattern is determined as the "agglutination pattern (+)", but if $\Delta E > V_1$ (FIG. 2), the pattern is judged to be the "non-agglutination pattern (−)". Furthermore, when the particle pattern has an intermediate agglutination as shown in FIGS. 3A, 3B and 3C, $V_2 \leq \Delta E \leq V_1$ is obtained and in such a case the pattern can be judged as an "intermediate pattern (?)". If a sample is judged to be the intermediate pattern (?), the sample is tested again so to improve the reliability of analysis.

However, the above explained known judging method has the following drawbacks. When the amount of particles contained in the reaction liquid is small, the integral pattern (−) has the configuration illustrated in FIGS. 4A and 4B and the particle amount distribution depicted in FIG. 4C. In such a case, the difference $\Delta E$ becomes small, because the number of the particles collected at the center of bottom is small. Then, $\Delta E \leq V_1$ and the pattern is erroneously determined as the intermediate pattern (?), and in an extreme case, the integral pattern might be judged as the uniform deposition pattern (+). Moreover, when the number of particles in the reaction liquid is too large, even in case of the agglutination reaction, many particles which could not be agglutinated roll down along the uniformly deposited particle layer and are collected at the center to form a particle pattern shown in FIGS. 5A, 5B and 5C. Then, the difference $\Delta E$ becomes larger than $V_2$ or $V_1$ and the pattern might be erroneously determined to be the intermediate patern (?) or the integral pattern (−) instead of the uniform deposition pattern (+).

Furthermore, as shown in FIGS. 6A, 6B and 6C, when the number of particles in the reaction liquid is too large and an unclear agglutination pattern is formed near the center portion due to a weak agglutination reaction, the agglutination pattern might be judged as the "integral pattern (−)" instead of the "intermediate pattern (?)", because $\Delta E$ becomes equal to that of the particle pattern shown in FIG. 2. Therefore, there occurs a drawback that a little particle agglutination reaction near the center portion is likely to be overlooked.

SUMMARY OF THE INVENTION

The present invention has for its object to provide a method for judging particle patterns which can obviate the above drawbacks of the known method and can determine accurately any kinds of particle patterns regardless of the amount of particles contained in a reaction vessel and/or the strength of the agglutination reaction.

According to the invention, a method of judging photoelectrically a particle agglutination pattern formed on an inclined bottom surface of a reaction vessel by particles descending on the bottom, comprises the steps of:

scanning the particle agglutination pattern formed on the inclined bottom surface of a reaction vessel to generate a plurality of photoelectrically converted output signals;

deriving a predetermined number of measurement values from said output signals; and effecting at least two judging steps on the basis of said measurement values to judge the particle agglutination pattern.

BRIEF DESCRIPTION OF THE DRAWINGS

FIG. 7 is a schematic view illustrating an embodiment of a particle pattern judging apparatus for carrying out the method according to the invention.

DESCRIPTION OF THE PREFERRED EMBODIMENTS

Figure 1A:
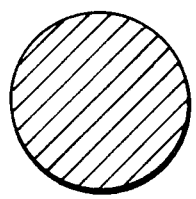
FIGS. 1A, 1B, 1C; 2A, 2B, 2C; 3A, 3B, 3C; 4A, 4B, 4C; 5A, 5B, 5C and 6A, 6B, 6C show configurations of six particle patterns formed on a conical bottom surface of a reaction vessel.

FIG. 7 is a schematic view showing an embodiment of a particle pattern judging apparatus for carrying out the method according to the invention. In the present embodiment, use is made of a microplate 1 made of transparent plastics and having a plurality of reaction vessels formed therein in a matrix form, each reaction vessel having a conically inclined bottom surface. The microplate 1 is uniformly illuminated by means of a light source 2, an illuminating lens 3 and a diffusion plate 4. An image of a conical bottom surface $1b$ of a reaction vessel $1a$ is formed by an imaging lens 5 onto a light receiving element 6. The light receiving element 6 is secured to a metal supporting member 9 which is engaged with a screw shaft 7 and is slidably mounted on a guide 8. Then, the screw shaft 7 is rotated by a motor 10 through gears 11 and 12 so as to move the light receiving element 6 in such a manner that a light receiving surface of the light receiving element 6 is moved linearly along the guide 8 so as to scan the inclined bottom surfaces $1b$ along a line passing through center portions (lowermost points) of successive reaction vessels $1a$. In this manner, according to the invention an image formed on the inclined bottom surface $1b$ of each reaction vessel $1a$ is scanned diametrically. In the present embodiment, an image of the bottom surface $1b$ having a diameter of about 12 mm which is two times larger than a diameter of the inclined bottom surface $1b$ is focused onto the light receiving element 6 by means of the enlargement imaging lens 5 and a dimension of the light receiving surface of the light receiving element 6 is about 0.5 mm × 0.5 mm. In such a case, a density of a part of the image of the inclined bottom surface $1b$ can be measured by the light receiving element 6 in a spot-like manner. Therefore, a density distribution of the image of the inclined bottom surface can be photoelectrically detected by linearly moving the light receiving element 6 in accordance with the rotation of the screw shaft 7. An output of the light receiving element 6 is supplied to a processing device 15 through an amplifier 13 and an A/D converter 14. In the processing device 15, a calculation explained below is made to this output so as to judge the agglutination pattern, and then a calculation result is indicated by a display device 16.

In the present invention, a distance between a scan start point and a scan end point on the inclined bottom surface is equidistantly divided into twenty-five measuring points $x_1, x_2, \ldots, x_{25}$ including the scan start and end points and outputs $e_1, e_2, \ldots, e_{25}$ corresponding to these measuring points are derived by sampling the outputs of the light receiving element 6. Now, if it is assumed that average transmittivities of a particle layer at respective measuring points are $k_1, k_2, \ldots, k_{25}$, total transmittivities of light paths except for the particle layer (test liquid, reaction vessel, etc.) are $k'_1, k'_2, \ldots, k'_{25}$, incident light intensities at respective measuring points are equally $I_0$, an amplification of the amplifier 13 is $A$ and photoelectric conversion coefficient of the light receiving element 6 is $K$, the following equation is obtained:

$$e_i = K \cdot A \cdot k_1 \cdot k'_i \cdot I_0$$

($i = 1, 2, \ldots, 25$).

When the amplification A of the amplifier 13 is so adjusted that the output $e_i$ becomes 100 mV in the case that the reaction vessel $1a$ contains the reaction liquid without particles, i.e. $k_i = 1$, the output $e_i$ at respective measuring points in the case that the vessel contains the reaction liquid with particles becomes as follows:

$$e_i = 100 k_i.$$

Figure 8A:
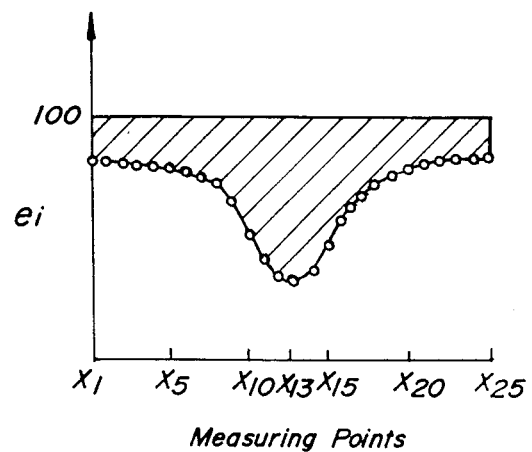
FIGS. 8A and 8B are graphs for explaining the judging method according to the invention by means of the apparatus shown in FIG. 7.
Figure 8B:
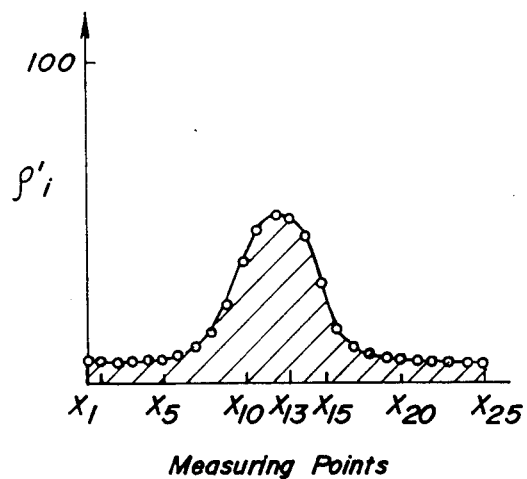

Moreover, the distribution of the output $e_i$ becomes as shown in FIG. 8A. Now, it is further defined that $\rho_i = 1 - k_i$. The $\rho_i$ is a measure of the light that does not transmit through at the respective measuring points due to the scattering and absorption by means of the particle layer deposited on the bottom surface. When $\rho_i$ is multiplied by 100, $\rho'_i = 100 \rho_i = 100 - 100 k_i = 100 - e_i$ can be obtained. The value of $\rho'_i$ represents a difference between the output of 100 mV in case of the reaction liquid without particles and the output $e_i$ in the case of the reaction liquid with particles. In other words, the value of $\rho'_i$ represents a percentage of the reduction in the output due to the existence of particles and thus is determined by a thickness of the particle layer at the respective measuring points. In this case, the distribution of $\rho'_i$ corresponding to the distribution of the output $e_i$ shown in FIG. 8A becomes as shown in FIG. 8B. The hatched areas shown in FIGS. 8A and 8B are equal to each other, and the amount thereof corresponds to the total particle amount.

In the present embodiment, three judging steps which will be explained hereinafter are performed by utilizing the $\rho'_i$ so as to judge the agglutination pattern.

(1) At first, a total sum $S$ of $$\rho'_i \left( S = \sum_{i=1}^{25} \rho'_i \right)$$

is derived. Since this total sum $S$ corresponds to the thickness of the particle layer at the respective measuring points, the total sum $S$ represents the total particle amount. Next, a density level of the deposited particle layer is judged by comparing the total sum $S$ with suitable reference values $S_1$ and $S_2$ ($S_1 > S_2$). When the amount of particles contained in the reaction vessel is too little or too large to form a correct agglutination pattern due to any reason, it is impossible to judge the particle pattern accurately. Therefore, the reference values $S_1$ and $S_2$ are experimentally determined corresponding to such extreme particle amounts and then the total sum $S$ is compared with these reference values $S_1$ and $S_2$ to judge the density level of the particle layer as follows:

$S > S_1$: D (dark)
$S_1 \geq S \geq S_2$: N (normal)
$S < S_2$: T (thin)

In this embodiment, when the density level is judged as dark (D) or thin (T), further judgement is not effected and the agglutination pattern is judged as an abnormal or questionable pattern "?". Contrary to this, when the density level is judged as normal (N), the judgement will be further proceeded. In this case, it is assumed that all the particle patterns shown in FIGS. 1 to 6 are judged as normal (N).

Figure 1B:
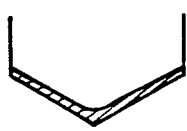
Figure 1C:
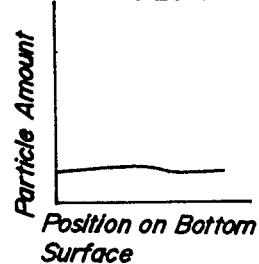
Figure 2A:
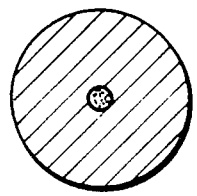
Figure 2B:
Figure 3A:
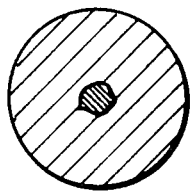
Figure 3B:
Figure 3C:
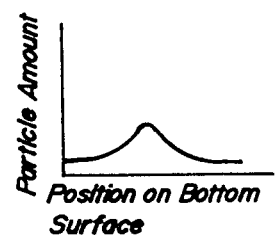
Figure 4A:
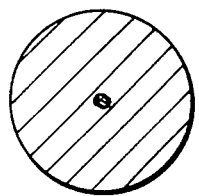
Figure 4B:
Figure 4C:
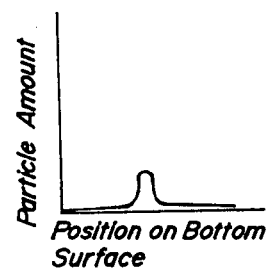
Figure 5A:
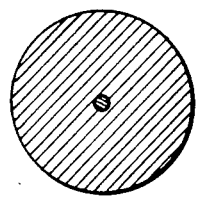
Figure 5B:
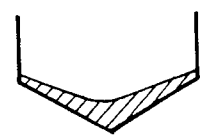
Figure 5C:
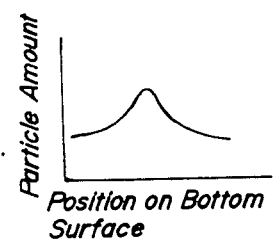

(2) In the next step, an average of values $\rho'_i$ at five measuring points $x_{11}$ to $x_{15}$ including the point $x_{13}$ which corresponds to the lowermost point of the inclined bottom surface $1b$ i.e. an average thickness $\rho'_c$ of the particle layer at the center portion of the bottom surface, and an average of values $\rho'_i$ at six measuring points $x_5$ to $x_7$ and $x_{19}$ to $x_{21}$ i.e. an average thickness $\rho'_p$ of the particle layer at the peripheral portion are calculated. At first, a ratio $r = \rho'_c / \rho'_p$ of these average thicknesses is calculated and then the ratio $r$ is compared with given reference values $R_1$ and $R_2$ ($R_1 > R_2$) which have been experimentally determined, where $R_1$ is the lowest value providing a definite reading of an integral pattern ($-$), and $R_2$ is the largest value providing a definite reading of a uniform deposition pattern ($+$). In this case, when a strong particle agglutination reaction occurs as shown in FIGS. 1 and 5 and a large number of particles remain on the peripheral portion of the bottom surface, the ratio $r$ between the averge thickness of the particle layer at the center portion and that at the peripheral portion becomes small. Moreover, when non-agglutination reaction occurs as shown in FIGS. 2, 4 and 6, the ratio r becomes large. Further, when the intermediate agglutination reaction occurs as shown in FIG. 3, the ratio r has an intermediate value. Therefore, by comparing the ratio r with the two reference values $R_1$ and $R_2$, the following judgements are effected.

$r > R_1$: "integral pattern (−)"
$R_1 \geq r \geq R_2$: "intermediate pattern (?)"
$r < R_2$: "uniform deposition pattern (+)"

Figure 6A:
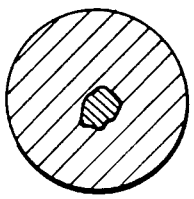
Figure 6B:

However, since the patterns shown in FIGS. 2 and 6 cannot be distinguished from each other even after the aforementioned two judging steps have been performed, it is necessary to effect the following third judging step.

Figure 2C:
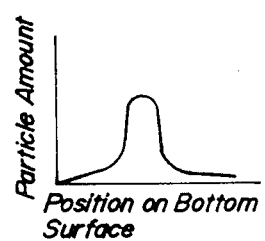
Figure 6C:
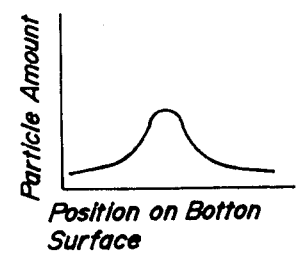

(3) As clearly understood from the FIGS. 2C and 6C, the patterns shown in FIGS. 2 and 6 are different in that the distribution of the particle amount i.e. the variation of $\rho'_i$ shown in FIG. 2 is more abrupt than that of FIG. 6. Therefore, in this step, first a difference between adjacent measuring points, i.e. an inclination of the distribution curve, is derived from $\Delta\rho_i = |\rho'_i - \rho'_{i+1}|$, and a first maximum value $\Delta\rho_{i1}$ among values $\Delta\rho_i$ between successive measuring points $x_1$ to $x_{13}$ and a second maximum value $\Delta\rho_{i2}$ among values $\Delta\rho_i$ between successive measuring points $x_{13}$ to $x_{25}$ are selected. Then, the average value between these first and second maximum values, i.e. the average maximum inclination, is derived from $\Delta\rho_{im} = (\Delta\rho_{i1} + \Delta phd i2)/2$. This $\Delta\rho_{im}$ is varied corresponding to the respective patterns shown in FIGS. 1 to 6. In this case, the $\Delta\rho_{im}$ in the case that the agglutination reaction occurs as shown in FIGS. 3, 5 and 6 becomes smaller than the $\Delta\rho_{im}$ in the case that non-agglutination reaction occurs as shown in FIGS. 2 and 4, and the $\rho_{im}$ in the case that the strong agglutination reaction occurs as shown in FIG. 1 becomes further smaller. Therefore, by comparing the average value $\Delta\rho_{im}$ with two reference values $H_1$ and $H_2$ ($H_1 > H_2$) which have been experimentally determined where $H_1$ is the lowest value providing a definite reading of an integral pattern (−), and $H_2$ is the largest value providing a definite reading of a uniform deposition pattern (+), the following judgements can be effected:

$\Delta\rho_{im} > H_1$: "integral pattern (−)"
$H_1 \geq \Delta\rho_{im} \geq H_2$: "intermediate pattern (?)"
$\Delta\rho_{im} < H_2$: "uniform deposition pattern (+)"

In the present invention, after effecting the first, second and third judging steps for the outputs $e_i$, a final judgement is performed on the basis of a table 1 described hereinafter. That is to say, when the density level is judged as D (dark) or T (thin) in the first judging step, the second and third judging steps are not applied to this pattern and the test liquid is judged as the indeterminate or abnormal state i.e. "intermediate pattern (?)". That is to say, the second and third judging steps are applied only to the test liquid whose density level is judged as N (normal) in the first judging step. Then, if the judgement results obtained by the second and third judging steps become identical with each other, the test liquid is finally judged in accordance with such results. In the other cases, the test liquid is judged to be indeterminate or abnormal and is indicated as the "intermediate pattern (?)". In this manner, even if the pattern shown in FIG. 6 is judged as the "integral pattern (−)" in the second judging step, it is judged as the "uniform deposition pattern (+)" in the third judging step and thus the final judgment becomes the "intermediate pattern (?)". Therefore, according to the invention, since all the inaccurate patterns can be judged as the "intermediate pattern (?)" and can be reexamined, the miss-judgement can be eliminated effectively.

TABLE 1

| (1) | (2) | (3) | Final judgement |
|---|---|---|---|
| T | | | ? |
| N | + | + | + |
|   |   | ? | ? |
|   |   | − | ? |
|   | ? | + | ? |
|   |   | ? | ? |
|   |   | − | ? |
|   | − | + | ? |
|   |   | ? | ? |
|   |   | − | − |
| D | | | ? |

The present invention is not limited to the embodiments mentioned above, but various alterations and modifications are possible. For example, in the embodiment mentioned above, the reaction vessels are formed in the microplate, but they may be constituted by separate reaction vessels. Moreover, the bottom surface of a reaction vessel may be formed in any desired shape such as a pyramid, gable roof shape and pentroof shape. Further, in the embodiment mentioned above, the bottom surface of a reaction vessel is illuminated uniformly to focus the image onto the imaging plane and the scanning operation is performed by moving the light receiving element having very little light receiving surface in the imaging plane. However, it is possible to effect the scanning operation by moving a spot light source for effecting a spot illumination in the bottom surface or by utilizing various other scanning methods such as using a linear array of image pick-up elements. Furthermore, in the second judging step, the average thicknesses of the particle layers at the center and peripheral portions on the bottom surface are respectively derived, but it is possible to judge the agglutination pattern corresponding to thicknesses at two measuring points respectively situated in the center and peripheral portions. Moreover, in the third judging step, the inclination is derived from the difference in thicknesses of the particle layer at adjacent measuring points, but it is possible to derive the inclination from difference in thicknesses at measuring points which are apart from each other by more than two points. Further, in the embodiment mentioned above, three judging steps are performed for the test liquid, but arbitrarily one step among them can be eliminated. In other words, according to the invention, it is necessary to effect at least two judging steps. Furthermore, as one judging step among them, use may be made of the judging method wherein the test liquid is judged on the basis of a difference between the photoelectric outputs at the center portion including the lowermost point of the bottom surface and at the peripheral portion thereof. Moreover, in the embodiments mentioned above, the number of sampling points are set at twenty five, but the sampling number can be set much larger or smaller.

As mentioned above, according to the invention, a plurality of sampling values are derived from the photoelectric conversion outputs obtained by scanning the image formed on the inclined bottom surface of the reaction vessel, and the agglutination pattern of the particle layer formed on the inclined bottom surface can be precisely judged by effecting at least two judging steps on the basis of the thus sampled output values.

Therefore, according to the invention, it is possible to always perform an accurate judgment.

What is claimed is:

1. A method of photoelectrically judging a particle agglutination pattern formed on an inclined bottom surface of a reaction vessel by particles descending on the bottom, comprising the steps of:

scanning the particle agglutination pattern formed on the inclined bottom surface of a reaction vessel to generate a plurality of photoelectrically converted output signals;

deriving from said output signals a predetermined number of measurement values representing the thickness at varying locations of a particle layer deposited on the bottom surface of the reaction vessel; and effecting a first judging step utilizing said measurement values by comparing said measurement values to at least two references values to judge the particle agglutination pattern and, if the result is not indeterminate, effecting at least one additional judging step utilizing said measurement values by comparing said measurement values to at least two reference values to judge the particle agglutination pattern.

2. A method according to claim 1, wherein one of said judging steps comprises deriving a ratio r between a first thickness of the particle layer at a first portion thereof, the first portion including the lowermost point of the bottom surface, and a second thickness at a second portion thereof remote from the first portion;

comparing said ratio r with two experimentally pre-determined reference values $R_1$ and $R_2$; and judging the particle agglutination pattern in the following manner:

$r > R_1$: integral pattern $(-)$
$R_1 \geq r \geq R_2$: intermediate pattern (?)
$r < R_2$: uniform deposition pattern $(+)$.

3. A method according to claim 1, wherein one of said judging steps comprises deriving a difference $\Delta E$ between measurement values at a first portion of the particle layer, said first portion including the lowermost point of the bottom surface, and at a second portion thereof remote from the first portion;

comparing the difference $\Delta E$ with two experimentally pre-determined reference values $V_1$ and $V_2$; and judging the particle agglutination pattern in the following manner:

$\Delta E > V_1$: integral pattern $(-)$
$V_1 \geq \Delta E \geq V_2$: intermediate pattern (?)
$\Delta E < V_2$: uniform deposition pattern $(+)$.

4. A method according to claim 1, wherein one of said judging steps comprises deriving an average maximum inclination $\Delta \rho_{im}$ from a distribution curve of the measurement values by averaging the two greatest inclinations between adjacent measurement values;

comparing said average maximum inclination $\Delta \rho_{im}$ with two experimentally pre-determined reference values $H_1$ and $H_2$; and judging the particle agglutination pattern in the following manner:

$\Delta \rho_{im} > H_1$: integral pattern $(-)$
$H_1 \geq \Delta \rho_{im} \geq H_2$: intermediate pattern (?)
$\Delta \rho_{im} < H_2$: uniform deposition pattern $(+)$.

5. A method according to claim 4, wherein the reaction vessel has a conical bottom surface and the inclination $\Delta \rho_{im}$ is derived as an average of two maximum inclinations obtained on respective sides of the distribution curve with respect to the center lowermost point.

6. A method according to claim 1, wherein one of said judging steps comprises deriving a total particle amount S from said measurement values;

comparing said total particle amount S with two experimentally pre-determined reference values $S_1$ and $S_2$; and judging the particle agglutination pattern in the following manner:

$S > S_1$: D (dark)
$S_1 \geq S \geq S_2$: N (normal)
$S < S_2$: T (thin).

7. A method according to claim 6, wherein said total particle amount S is derived by summing of all the measurement values.

8. A method according to claim 6, wherein when said particle agglutination pattern is judged as D or T in the first judging step the result is indeterminate, the further judging steps are not applied to this pattern and said particle agglutination pattern is judged as an intermediate pattern (?).

9. A method of judging photoelectrically a particle agglutination pattern formed on a conically-inclined bottom surface of a reaction vessel by particles precipitating onto the bottom, comprising the steps of:

scanning the particle agglutination pattern formed on the inclined bottom surface to generate a plurality of photoelectrically converted output signals representative of the thickness of the particle layer precipitated onto the bottom surface at a corresponding plurality of locations;

subjecting the output signals to a first judging step comprising:

summing said plurality of output signals to determine a total absorption S;

experimentally determining the maximum total absorption $S_1$ and the minimum total absorption $S_2$ for which reliable pattern analysis may be conducted;

comparing said total absorption S with the two experimentally determined reference values $S_1$ and $S_2$, and judging the particle agglutination pattern as follows:

$S > S_1$: D (dark)
$S_1 \geq S \geq S_2$: N (normal)
$S < S_2$: T (thin)

if S is judged D (dark) or T (thin), outputting a signal indicating an indeterminate agglutination, and otherwise proceeding to a second judging step comprising:

deriving a ratio r between a first group of output signals representing the thickness of the particle layer at a first portion thereof over the lowermost point of the bottom surface, and a second group of output signals representing a second portion of the layer remote from the first portion;

experimentally determining the ratio $R_1$ which is the minimum ratio which reliably indicates an integral pattern, and the ratio $R_2$ which is the maximum ratio which reliably indicates a uniform deposition pattern;

comparing said ratio r with the two experimentally determined reference values $R_1$ and $R_2$ and judging the particle agglutination pattern as follows:

$r > R_1$: integral pattern (−)
$R_1 \geq r \geq R_2$: intermediate pattern (?)
$r < R_2$: uniform deposition pattern (+)

if r is judged to have an intermediate pattern, outputting a signal indicating an indeterminate agglutination, and otherwise proceeding to a third judging step comprising:

determining the two greatest values of inclination between output signals representing adjacent locations and averaging the two signals to produce an average maximum inclination $\Delta\rho_{im}$;

experimentally determining the minimum inclination $H_1$ which reliably indicates an integral pattern and the maximum inclination $H_2$ which reliably indicates a uniform deposition pattern;

comparing said inclination $\Delta\rho_{im}$ with the two experimentally determined reference values $H_1$ and $H_2$ and judging the particle agglutination pattern as follows:

$\Delta\rho_{im} > H_1$: integral pattern (−)
$H_1 \geq \Delta\rho_{im} \geq H_2$: intermediate pattern (?)
$\Delta\rho_{im} < H_2$: uniform deposition pattern (+);

if $\Delta\rho_{im}$ is judged to have an intermediate pattern, or if $\Delta\rho_{im}$ is judged to have an integral pattern when r was judged to have a uniform deposition pattern, or if $\Delta\rho_{im}$ is judged to have a uniform deposition pattern when r was judged to have an integral pattern, outputting a signal indicating an indeterminate agglutination, and if both r and $\Delta\rho_{im}$ are judged to have an integral pattern, outputting a signal indicating an integral pattern, and if both r and $\Delta\rho_{im}$ are judged to have a uniform deposition pattern, outputting a signal indicating a uniform deposition pattern.

10. A method according to claim 9, wherein 25 output signals are generated.

11. A method according to claim 10, wherein r is determined by:

producing a first signal representing the first group of output signals by averaging the output signals at the five points ($x_{11}$ to $x_{15}$) centered around the lowermost point of the inclined bottom surface;

producing a second signal representing the output signals in the second group by averaging six output signals taken from points on either side of the lowermost point, spaced apart both from the first group and from an edge of the field tested ($x_5$ to $x_7$ and $x_{19}$ to $x_{21}$); and determining the ratio of the first signal to the second signal.

* * * * *